United States Patent [19]

Cookson et al.

[11] 4,035,499
[45] July 12, 1977

[54] IMIDAZO (1,2-b) ISOQUINOLINE DERIVATIVES

[75] Inventors: Ronald Frederick Cookson; David Peter Nowotnik, both of Reading, England

[73] Assignee: Aspro-Nicholas Limited, Slough, England

[21] Appl. No.: 627,906

[22] Filed: Oct. 31, 1975

[30] Foreign Application Priority Data

Nov. 5, 1974 United Kingdom ............ 47801/74

[51] Int. Cl.$^2$ ................ C07D 471/04; A61K 31/47
[52] U.S. Cl. .......................... 424/258; 260/283 S; 260/283 SA; 260/287 CF; 260/287 D; 260/288 CF; 260/288 D; 260/289 B
[58] Field of Search ............... 260/288 CF, 287 CF, 260/283 S, 283 SA; 424/258

[56] References Cited
PUBLICATIONS

Burger; Medicinal Chemistry 2nd Edition, (1960), p. 42,497; 3rd Edition (1970) p. 1588.
Cookson et al; J. Chem. Soc., Chem Comm., (1974) p. 911-912.
Krohnke et al; Chem. Ber. vol. 95, (1962) p. 1128.

*Primary Examiner*—Donald G. Daus
*Assistant Examiner*—Mary C. Vaughn
*Attorney, Agent, or Firm*—Foster York

[57] ABSTRACT 5,10-Dihydro-imidazo(1,2b)isoquinolines substituted in the 2- and/or 3-position(s) by an aromatic group have analgesic, anti-inflammatory or anti-pyretic activity. Except for 2-phenyl-5,10-dihydroimidazo(1,2-b)isoquinoline, they are believed to be novel compounds. They can be prepared in manner known per se by heating a 2-acylmethyl isoquinolinium salt with an ammonium salt of an organic acid or by reaction of a 3-amino-1,4-dihydroisoquinoline with an α-halogenocarbonyl compound.

13 Claims, No Drawings

IMIDAZO (1,2-B) ISOQUINOLINE DERIVATIVES

The present invention relates to imidazo(1,2-b)isoquinoline derivatives and provides pharmaceutical compositions containing them. The invention provides also certain of said derivatives per se and methods of preparing the derivatives.

According to one embodiment of the present invention, there are provided pharmaceutical compositions comprising, in association with a carrier or diluent, a pharmacologically active 5,10-dihydro-imidazo(1,2-b)isoquinoline substituted in at least one of the 2 and 3 positions by an aromatic group, i.e. compounds of the formula I: -

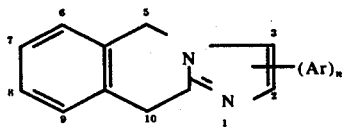

wherein n represents 1 or 2 and
Ar represents an aromatic group attached by a ring carbon atom thereof to the 2 or 3 position of the dihydroimidazoisoquinoline nucleus and, when n represents 2, the groups can be the same or different, or a pharmacologically acceptable acid addition salt thereof.

The compounds of formula I are believed to be novel with the exception of the compound in which n represents 1 and Ar represents unsubstituted phenyl in the 2-position of the dihydroimidazoisoquinoline nucleus, i.e., 2-phenyl-5,10-dihydro-imidazo-(1,2b)isoquinoline. The said known compound is prepared by the method disclosed in a paper Kroehnke and Zecher (Chem. Ber., 1962, 95, 1128 ) although that paper incorrectly identifies the product. Said product has only recently been correctly identified by Cookson, Nowotnik and Parfitt (J. Chem. Soc., Chem. Comm., to be published).

According to another embodiment of the present invention therefore, there are provided pharmacologically active 5,10-dihydroimidazo(1,2b)isoquinolines substituted in at least one of the 2 and 3 positions by an aromatic group, provided that when there is an aromatic group in the 2 position but not the 3 position, that group is not unsubstituted phenyl, and acid addition salts and quaternary ammonium derivatives thereof.

The aromatic group(s) in the 2 and/ or 3 positions can be carbocyclic or heterocyclic and are directly attached to the dihydro-imidazoisoquinoline nucleus by a ring carbon atom. Preferred aromatic groups are those having a furyl, thienyl, pyridyl or, especially, phenyl ring. The ring of the aromatic group can be substituted by one or more "therapeutically compatible" (as hereinafter defined) substituents. When the aromatic group is phenyl, especially suitable substituents are $C_1-C_4$ alkoxy groups which preferably are in the para-position relative to attachment of the ring to the dihydro-imidazoisoquinoline nucleus. Other suitable substituents include methylenedioxy, $C_1-C_4$ alkyl, primary amino, $C_1-C_4$ alkylamino, di($C_1-C_4$ alkyl)amino, halogen, trifluoromethyl, and $C_1-C_4$ acylamino.

The dihydro-imidazoisoquinoline nucleus can be substituted in any one or more of the 5, 6, 7, 8, 9, 10 and, if available, 2 or 3 positions by "therapeutically compatible" (as hereinafter defined) substituents. Usually, there will be at least one hydrogen atom at each of the 5 and 10 positions because the preferred method of preparation results in one hydrogen atom at each of said positions.

The term therapeutically compatible is used in this specification in relation to a substituent to mean that the presence of that substituent neither destroys the pharmacological activity of the molecule nor so decreases said acitity and/or increases the toxicity of the molecule that the therapeutic ratio is reduced to five or below. The therapeutic compatibility of a particlar substituent may depend upon the intended site of substitution in the molecule and/or the presence in the molecule of other substituents. Hence a given substituent may be therapeutically compatible in respect of one molecule into which it is to be introduced but incompatible, i.e., inactivating, in respect of another molecule. The compatibility of any substituent in respect of any molecule having formula I can readily be assessed by subjecting the relevant compound to standard screening tests such as those referred to hereinafter. It is well within the ability of the average skilled man concerned with the development of new drugs to ascertain which substituents may be present in pharmacologically active compounds of formula I.

Examples of substituents which are likely to be therapeutically compatible with most, if not all, of the compounds of formula I both in the nucleus and the aromatic group substituent(s) are alkyl, alkoxy, halogen, halogenoalkyl, hydroxy, hydroxyalkyl, alkylthio, alkylsulphinyl, alkylsulphonyl, primary amino, alkylamino, dialkylamino, acylamino, nitro, alkylsulphonamido (i.e., alkyl. $SO_2$—NH—) and sulphamoyl (i.e., $H_2N.SO_2$) wherein each alkyl moiety contains 1 to 6 carbon atoms.

A preferred class of compounds of formula I are those of formula II:

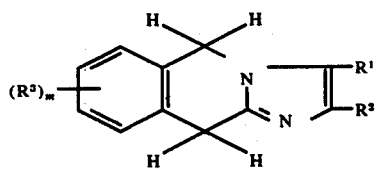

wherein
$R^1$ and $R^2$ independently represent phenyl optionally substituted by methylenedioxy, $C_1-C_4$ alkyl, primary amino, $C_1-C_4$ alkyl amino, di($C_1-C_4$ alkyl)amino or halogen, trifluoromethyl, $C_1-C_4$ acylamino, or preferably, $C_1-C_4$ alkoxy; hydrogen or the group $R_3$, provided that at least one of $R^1$ and $R^2$ is substituted or unsubstituted phenyl;

m represents 0 or an integer up to 6, especially 0, 1 or 2; and $R^3$ represents alkyl, alkoxy, halogen, halogenoalkyl, hydroxy, hydroxyalkyl, alkylthio, alkylsulphinyl, alkylsulphonyl, primary amino, alkylamino, dialkylamino, acylamino, nitro, alkylsulphonamido or sulphamoyl, wherein each alkyl moiety contains 1 to 6 carbon atoms.

An especially preferred class of compounds of formula I are those of formula III:

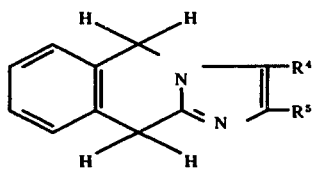

III wherein
R[4] and R[5] independently represent phenyl optionally substituted by methoxy, preferably in the para-position, or hydrogen provided that at least one of R[4] and R[5] is phenyl or methoxyphenyl.

Specific examples of said compounds of formula III are:
A. 2-phenyl-5,10-dihydroimidazol(1,2b)isoquinoline;
B. 2,3-diphenyl-5,10-dihydroimidazo(1,2b)isoquinoline; and
C. 2,3-di(p-methoxy phenyl)-5,10-dihydroimidazo(1,2b)isoquinoline.

The compounds of formula I have been found to possess valuable pharmacological properties, in particular analgesic, anti-inflammatory and/or anti-pyretic activity as determined by the phenylbenzoquinone abdominal constriction test (as described by Parkes and Pickens in Brit. J. Pharmacol, Chemother., 1964, 25, 81). An indication of the potential value of the compounds is provided by comparing the PD50 (i.e., the dose reducing the number of writhes by 50%) p.o. doses for the compounds (A), (B) and (C) above and for the known analgesic/anti-pyretic drug paracetamol and their respective lethalities at 512 mg/kg p.o. The relevant figures are set forth in Table 1.

Table 1

| Compound | PD50 mg/kg p.o. | Lethality at 512 mg/kg p.o. |
|---|---|---|
| A | 275 | None |
| B | 62.7 | None |
| C | 5.1 | None |
| Paracetamol | 128 | 60% |

The compounds of formula I can be prepared from the corresponding isoquinoline in two steps. Firstly, the isoquinoline is quaternised in manner known per se to the appropriate 2-acylmethyl isoquinolinium salt, which step can be represented as follows:

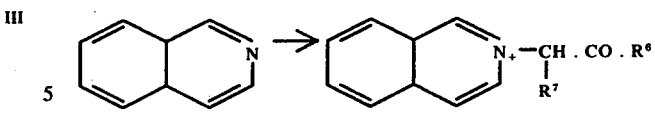

wherein at least one of R[6] and R[7] is the aromatic group desired in the 2 or 3 position respectively of the dihydroimidazoisoquinoline to be prepared and, if there is to be only one such aromatic group in said final product, the other of R[6] and R[7] is hydrogen or a substituent group which is inert under the reaction conditions of the second step (see below) to the extent that it does not prevent the desired ring closure of said second step. Suitably, the quaternisation can be effected using an α-halogenocarbonyl compound of the formula R[6].CO.CHR[7]X, where X is halogen especially bromine, or a derivative thereof such as an acetal or ketal. In the case where R[6] is hydrogen, it may be necessary to protect the carbonyl group in the quaternising agent by, for example, acetyl formation to avoid competing reactions. The quaternary salt produced by the first step can be isolated if desired or used in its crude form as prepared.

The second step consists of heating the quaternary salt intermediate in manner known per se with the ammonium salt of an organic acid in the presence of a polar protic solvent. Preferably the organic acid is a carboxylic acid, especially acetic acid. Suitable solvents are methanol and, preferably, acetic acid. It is advantageous to perform the reaction under reflux conditions. The second step can be represented as follows:

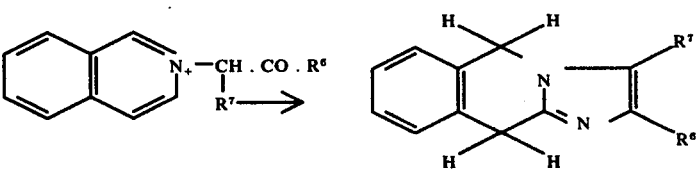

Alternative methods of preparing the compounds of formula I will be readily apparent to those skilled in the art. For example when a compound of formula I having two substituents at the 5 and/or 10 position is required, the corresponding 3-amino-1,4-dihydroisoquinoline could be reacted in manner known per se with an α-halogenocarbonyl compound in accordance with the following representation:

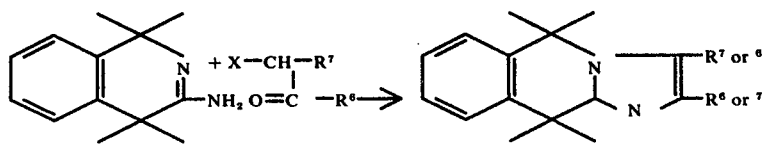

The processes described above may be employed to prepare all of the compounds of the present invention although in some cases direct formation of a particular compound by one or more of said processes may not be possible. However, it will be readily apparent to those skilled in the art that those compounds which cannot be prepared directly by the said process or processes may be obtained by methods known per se from related compounds. These conversions are carried out by methods well known per se. Thus, for example, a hydroxyalkyl substituent may be converted to a halogenoalkyl substituent by reaction with a halogenating agent such as thionyl chloride or phosphorus tribromide in the presence of an inert solvent such as chloroform.

The compounds produced by the foregoing process may be isolated either per se or as acid addition salts or quaternary ammonium derivatives thereof.

The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, malic, tartaric, citric, salicylic, o-acetyloxybenzoic, nicotinic or isonicotinic, or organic sulphonic acids for example methane sulphonic, ethane sulphonic, 2-hydroxyethanesulphonic, toluene-p-sulphonic, or napthalene-2-sulphonic acids. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the bases.

A resulting acid addition salt may be converted into the free compound according to known methods, for example, by treating it with a base, such as with a metal hydroxide or alkoxide, for example an alkali or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exhange preparation, or with any other suitable reagent.

A resulting acid addition salt may also be converted into another acid addition salt according to known methods; for example, a salt with an inorganic acid may be treated with a metal salt, for example a sodium, barium or silver salt, or an acid in a suitable diluent, in which a resulting inorganic salt is insoluble and is thus removed from the reaction medium. An acid addition salt may also be converted into another acid addition salt by treatment with an anion exchange preparation.

Quaternary ammonium derivatives of the compounds of this invention are particularly those formed by reaction with lower alkyl halides, for example, methyl, ethyl, or propyl chloride, bromide or iodide; di-lower alkyl sulphates, for example, dimethyl or diethyl sulphate; lower alkyl lower alkane sulphonates for example, methyl or ethyl methane sulphonate or ethane sulphonate; lower alkyl aryl sulphonates, for example methyl or ethyl p-toluene sulphonates; and phenyl-lower alkyl halides, for example benzyl or phenethyl chloride, bromide or iodide. Also included are the quaternary ammonium hydroxides and the quaternary ammonium compounds having as anions those of other inorganic or organic acids, for example those of the acids used for the preparation of the previously mentioned acid addition salts.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a carrier, or enclosed or encapsulated in a capsule, sachet, cachet, paper or other container. A carrier or diluent may be solid, semi-solid or liquid material which serves as a vehicle, excipient or medium for the active ingredient. Some examples of such diluents or carriers ae lactose, dextrose, sucrose, sorbitol, mannitol, starches, gum acacia, calcium phosphate, liquid paraffin, cocoa butter, oil of theobroma, alginates, tragacanth, gelatin, syrup B.P., methyl cellulose, polyoxyethylene sorbitan monolaurate, methyl- and propyl-hydroxybenzoate, talc, magnesium stearate or mineral oil.

The formulations of the invention may be adapted for enteral or parenteral use and may be administered to a subject requiring treatment, for example an animal suffering an inflammatory condition, in the form of tablets, capsules, suppositories, solutions, suspensions or the like. The dosage required for the treatment of any animal will usually fall within the range of 0.01 to 250 mg/kg. For example in the treatment of adult humans, each dosage of active ingredient is expected to be from 0.01 to 15 mg/kg, whereas in the treatment of test animals such as mice and rabbits a dosage of 10 to 200 mg/kg may be used. The formulations of the invention may therefore be provided in dosage unit form, preferably each dosage unit containing from 1 to 1000 mg., more advantageously from 5 to 500 mg., and most preferably from 10 to 250 mg of the active ingredient of the invention.

It will be appreciated that in the case of the known compound of formula I referred to above, we do not include within the scope of pharmaceutical compositions comprising that compound mere solutions of it in ordinary water or a common non-toxic organic solvent where such solutions are not in unit dosage forms. However, said scope does include formulations of the known compound in, for example, pyrogen-free water or a substantially isotonic saline solution.

The term "dosage unit form" is used herein to mean a physically discrete unit containing an individual quantity of the active ingredient in admixture with or otherwise in association with the carrier, said quantity being such that one or more units are normally required for a single therapeutic administration or that, in the case of severable units such as scored tablets, at least one fraction such as half or quarter of a severable unit is required for a single therapeutic administration.

The following Examples will further illustrate the present invention. All temperatures are given in degrees Centigrade.

EXAMPLE 1

A. 2-phenacylisoquinolinium bromide

A solution of phenacyl bromide (20 g) in dry ether (100 ml) was added, with stirring, to a solution of isoquinoline (13 g) in ether (50 L ml). The solution was stirred for 30 minutes, and allowed to stand overnight. The precipitated product was filtered off, washed well with ether, and dried. Yield 26.8 g.

B. 5,10-dihydro-2-phenylimidazo(1,2-b)isoquinoline

A solution of 2-phenacylisoquinolinium bromide prepared as above (13.1 g) and ammonium acetate (28 g) in glacial acetic acid (36 ml) was heated under reflux for 2 hours. The cooled reaction mixture was poured, with stirring, into water (600 ml). The resultant solid was filtered off and washed well with water. The solid was dissolved in methanol (20 ml), and added dropwise, with stirring, to a solution of sodium hydroxide (1.6 g) in water (100 ml). A further 300 ml of water was added to the suspension, and the granulated solid filtered off, washed well with water, dried, and crystallised from methanol. Yield 2.1 g (21%) m.p. 195°–197°. (Found C 82.8; H 6.0; N 11.4, Required C 82.9; H 5.7; N 11.4).

EXAMPLE 2

A. Desylisoquinolinium bromide

A solution of isoquinoline(10 g) and desylbromide (10 g) in dry benzene (50 ml) was stirred at 40° for seven hours. The suspension was allowed to stand overnight, and the benzene solution decanted off. The solid was ground to a powder, washed well with ether, and dried. Yield 12.3 g (85%), m.p. 239°–241° (Found C 68.3; H 4.6; N 3.4, Required C 68.3; H 4.5; N 3.5).

B. 5,10-dihydro-2,3-diphenylmidazo(1,2-b)isoquinoline

A solution of desylisoquinolinium bromide propared as above (11.5 g) and ammonium acetate (23.2 g) in glacial acetic acid (30 ml) was heated under reflux for three hours. The cooled solution was taken up in methanol (50 ml), and the methanolic solution added dropwise, with stirring, to a solution of 10N NaOH (50 ml) in water (600 ml). The resultant solid was filtered off, washed well with water, dried and crystallised from industrial methylated spirits. Yield 4.7 g (49%). m.p. 182°–184° (Found C 85.3; H 5.7; N 8.6, Required C 85.7; H 5.6; N 8.7;).

EXAMPLE 3

A. (4,4'-dimethoxydesyl)isoquinolinium bromide

A solution of α-bromodeoxy-p-anisoin (12 g) in isoquinoline (12 g) was heated in an oil bath at 160°0 for 10 minutes. The cooled reaction mixture was taken up in chloroform (50 ml), and the chloroform solution added dropwise, with stirring, to ether (600 ml). The suspension was stirred for 30 minutes, and the solid filtered off, washed well with ether and dried. Yield 18.0 g.

B. 5,10-Dihydro-2,3-bis(p-methoxyphenyl)imidazo(1,2-b)isoquinoline

A solution of the quarternary salt prepared as above (17.9 g) and ammonium acetate (31.3 g) in glacial acetic acid (40 ml) was heated under reflux for 2 hours. The cooled reaction mixture was poured, with stirring into a solution of 4N NaOH (100 ml) in water (500 ml). The resultant oil was dissolved in chloroform (200 ml), and the chloroform solution separated off, washed well with water, dried and concentrated. The residue was crystallised from industrial methylated spirits. Yield 6.4 g, m.p. 170°–172°; (Found C, 78.2; H, 5.6; N, 7.2; $C_{25}H_{22}N_2O_2$ Required C, 78.5; H, 5.7; N, 7.3%).

EXAMPLE 4

A. (4-Methoxyphenacyl) isoquinolinium bromide

The procedure of Example 1, Step A was repeated using 4-methoxyphenacyl bromide to give the isoquinolinium salt identified above.

B. 5,10-Dihydro-2(4'-methoxyphenyl)imidazo(1,2-b)isoquinoline

The procedure of Example 1, Step B was repeated using the isoquinolinium salt prepared as above and industrial methylated spirits instead of methanol as the recrystallising solvent to give 5,10-dihydro-2(4'-methoxyphenyl)imidazo (1,2-b)isoquinoline (m.p.260° dec).

EXAMPLE 5

A. α-(4'Methoxybenzoyl)benzyl isoquinolinium bromide

The procedure of Example 2, Step A was repeated using 2-bromo-2-phenyl-4'methoxyacetophenone to give the isoquinolinium salt identified above.

B. 5-10-Dihydro-2(4'-methoxyphenyl)-3-phenyl-imidazo(1,2-b) isoquinoline

The procedure of Example 2, Step B was repeated using the isoquinolinium salt prepared as above to give 5,10-dihydro-2(4'methoxyphenyl)-3-phenyl-imidazo(1,2-b)isoquinoline (m.p.172°–173°).

EXAMPLE 6

A. α-Benzoyl-4'-methoxybenzyl isoquinolinium bromide

The procedure of Example 2, Step A was repeated using 2-bromo-2-(4'-methoxyphenyl)-acetophenone to give the isoquinolinium salt identified above.

B. 5,10-Dihydro-2-phenyl-3-(4'-methoxyphenyl)imidazo(1,2-b) isoquinoline

The procedure of Example 2, Step B was repeated using the isoquinolinium salt prepared as above to give 5,10-dihydro-2-phenyl-3-(4'-methoxyphenyl)imidazo(1,2-b)isoquinoline (m.p. 183°–85°).

EXAMPLE 7

A. 2-(4,4'-Dichlorodesyl)isoquinolinium bromide

A solution of α-bromo-4,4'-dichlorodeoxybenzoin (20g) in diethylether (100ml) was added to a stirred solution of isoquinoline (20g) in diethylether (200ml). The mixture was allowed to stand for 18 hours and the resultant precipitated solid was filtered, washed with diethylether and dried to provide the isoquinolinium salt referred to above (yield 25.8g).

The benzoin starting material can be prepared by adding bromine (18.1g) dropwise to a stirred solution of 4,4'-dichlorodeoxybenzoin (30g) in dry diethylether (400ml). The solution is stirred for a further hour and evaporated to provide crude α-bromo-4,4'-dichlorodeoxybenzoin (40g) which when recrystallised from methanol has a melting point of 81°–83°.

4,4'-Dichlorodeoxybenzoin can be prepared by heating 4-chlorophenylacetic acid (85g) in thionyl chloride (59.5g) under reflux for 2.5 hours to yield 4-chlorophenylacetyl chloride (45.5g) which is subsequently dissolved in chlorobenzene (30g) and added dropwise with cooling to a stirred aluminium chloride (73g). The resultant mixture is cooled and stirred for a further 0.5 hours and then heated at 100° for one hour. The mixture was again cooled and poured into a mixture of conc. hyrochloric acid (200ml) and ice (1 liter) precipitate on standing crude 4,4'-dichlorodeoxybenzoin which on recrystallisation from methanol has a melting point of 115°–116°.

B. 2,3-Bis (p-chlorophenyl)-5,10-dihydroimidazo (1,2-b) isoquinoline

A solution of 2-(4,4'-dichlorodesyl)isoquinolinium bromide (20g) prepared as above and ammonium acetate (30g) in glacial acetic acid (38ml) was heated under reflux for 4 hours. The solution was cooled, poured into a stirred solution of ION sodium hydroxide solution (50ml) in water (500ml) and the resultant oil was dissolved in chloroform (100ml). The chloroform solution was washed with water and dried, the dried solution treated with ethereal hydrogen chloride (25ml) and the resultant solution added dropwise to stirred diethyl ether (500ml). The precipitated solid was filtered, washed with diethyl ether, dried and crystallised from isopropylalcohol to yield 2.8g of 2,3-bis (p-chlorophenyl)-5,10dihydroimidazo(1,2-b)isoquinoline as its hydrochloride (m.p.277°–280°).

In the following Examples relating to pharmaceutical compositions, the term "medicament" is used to indicate the compound 1,3-di(p. methoxy phenyl)-5,10-dihydro-imidazo (1,2-b)isoquinoline. This compound may be replaced in these compositions by any other anit-inflammatory compound of the invention, for example by 2,3-diphenyl- or 2-phenyl-5,10-dihydro-imidazo-isoquinoline. Adjustments in the amount of medicament may be necessary or desirable depending upon the degree of activity of the medicament as is well known in the art.

EXAMPLE 8 - Tablet formulation

| | mg/tablet |
|---|---|
| Medicament | 15 |
| Lactose | 86 |
| Maize Starch (dried) | 45.5 |
| Gelatin | 2.5 |
| Magnesium stearate | 1.0 |

The medicament is powdered and then passed through a B.S. No. 100 sieve and mixed well with the lactose and 30 mg of the maize strach, both passed through a B.S. No. 44 sieve.

The mixed powders are massed with a warm gelatin solution prepared by stirring the gelatin in water and heating to form a 10% w/w solution. The mass is granulated by passing through a B.S. No. 12 sieve and the moist granules dried at 40°.

The dried granules are re-granulated by passing through a B.S. No. 14 sieve and the balance of the starch sieved 44 mesh and the magnesium stearate sieved 60 mesh are added and thoroughly mixed.

The granulates are compressed to produce tablets each weighing 150 mg.

EXAMPLE 9 - Tablet formulation

| | mg/tablet |
|---|---|
| Medicament | 100 |
| Lactose | 39 |
| Maize starch (dried) | 80 |
| Gelatin | 4.0 |
| Magnesium stearate | 2.0 |

The method of preparation is identical with that of Example 8 except that 60 mg of starch is used in the granulation process and 20 mg during tabletting.

EXAMPLE 10 - Capsule formulation

| | mg/capsule |
|---|---|
| Medicament | 250 |
| Lactose | 150 |

The medicament and lactose are passed through a No. 44 B.S. sieve and the powders well mixed together before filling into hard gelatin capsules of suitable size, so that each capsule contains 400 mg of mixed powders.

EXAMPLE 11 - Suppositories

| | mg/suppository |
|---|---|
| Medicament | 50 |
| Oil of Theobroma | 950 |

The medicament is powdered and passed through a B.S. No. 100 Sieve and triturated with molten oil of Theobroma at 45° C to form a smooth suspension. The mixture is well stirred and poured into moulds each of nominal 1G capacity, to produce suppositories.

EXAMPLE 12 Cachets

| | mg/cachet |
|---|---|
| Medicament | 100 |
| Lactose | 400 |

The medicament is passed through a B.S. No. 40 mesh sieve, mixed with lactose previously sieved 44 mesh and filled into cachets of suitable size so that each contains 500 mg.

EXAMPLE 13 - Intramuscular Injection (suspension in aqueous vehicle)

| | | |
|---|---|---|
| Medicament | | 10 mg |
| Sodium Citrate | | 5.7 mg |
| Sodium carboxymethylcellulose (low viscosity grade) | | 2.0 mg |
| Methyl para-hydroxybenzoate | | 1.5 mg |
| Propyl para-hydroxybenzoate | | 0.2 mg |
| Water for Injection | to | 1.0 ml |

The sodium citrate and sodium carboxymethylcellulose are mixed with sufficient water for injection at 80°. The mixture is cooled to 50° and the methyl and propyl papr-hydroxybenzoate added followed by the medicament previously milled and sieved 300 mesh. When cool the injection is made up to volume and sterilized by heating in an autoclave.

We claim:

1. A pharmaceutical dosage unit composition consisting essentially of an analgesic, anti-inflammatory, or anti-pyretic effective amount of a 5,10-dihydroimidazo (1,2b) isoquinoline of the formula

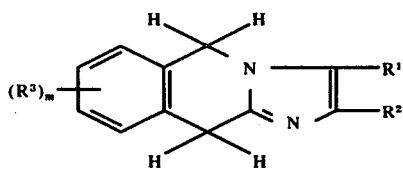

wherein
R¹ and R² independently represent phenyl, phenyl mono substituted by methylenedioxy, $C_1-C_4$ alkyl, $NH_2$, $C_1-C_4$ -alkylamino, di($C_1-C_4$ alkyl)amino, halogen, trifluoromethyl, $C_1-C_4$ alkanoylamino or $C_1-C_4$ alkoxy; hydrogen or the group R³ provided that at least one of R¹ and R² is phenyl or one of said substituted phenyls, m represents 0 or an integer up to 4, R³ represents alkyl, alkoxy, halogen, halogenalkyl, hydroxy, hydroxyalkyl, alkylthio, alkylsulphinyl, alkylsulphonyl, $NH_2$, alkylamino, dialkylamino, alkanoylamino, nitro, alkylsulphonamido or sulphamoyl, wherein each alkyl moiety has 1 to 6 carbon atoms or a pharmacologically acceptable nontoxic acid addition salt thereof, and a pharmaceutically acceptable carrier therefore.

2. A composition as claimed in claim 1 wherein R¹ and R² independently represent hydrogen, unsubstituted phenyl or $C_1-C_4$ alkoxyphenyl provided that at least one of them is phenyl or alkoxyphenyl.

3. A composition as claimed in claim 2 wherein the 5,10-dihydroimidazo(1,2b)isoquinoline is of the formula

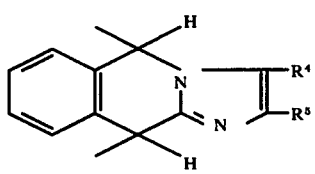

III wherein
R⁴ and R⁵ independently represent phenyl, methoxyphenyl or hydrogen provided that at least one of them is phenyl or methoxyphenyl
or a pharmacologically acceptable nontoxic acid addition salt thereof.

4. A composition as claimed in claim 3 wherein R⁴ and R⁵ independently represent phenyl, paramethoxyphenyl or hydrogen provided that at least one of them is phenyl or paramethoxyphenyl.

5. A composition as claimed in claim 4 wherein the active compound is 2-phenyl-5,10-dihydroimidazo(1,2b)isoquinoline; 2,3-diphenyl-5,10-dihydroimidazo(1,2b)isoquinoline; or 2,3-di-(paramethoxyphenyl)-5,10-dihydroimidazo(1,2b)isoquinoline.

6. A compound of the formula

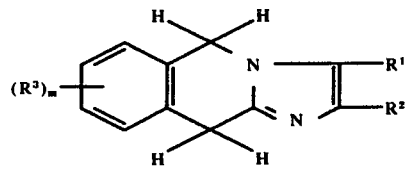

wherein
R¹ and R² independently represent phenyl, or phenyl mono substituted by methylenedioxy, $C_1-C_4$ alkyl, $NH_2$, $C_1-C_4$ -alkylamino, di($C_1-C_4$ alkyl)amino, halogen, trifluoromethyl, $C_1-C_4$ alkanoylamino or $C_1-C_4$ alkoxy; hydrogen or the group R³ provided that at least one of R¹ and R² is one of said substituted phenyl or unsubstituted phenyl, and provided that when there is an aromatic group in the 2 position but not in the 3 position, the group in the 2 position is not an unsubstituted phenyl, m represents 0 or an integer up to 4, R³ represents alkyl, alkoxy, halogen, halogenoalkyl, hydroxy, hydroxyalkyl, alkylthio, alkylsulphinyl, alkylsulphonyl, $NH_2$, alkylamino, dialkylamino, alkanoylamino, nitro, alkylsulphonamido or sulphamoyl, wherein each alkyl moiety has 1 to 6 carbon atoms or a pharmacologically acceptable nontoxic acid addition salt thereof.

7. A compound as claimed in claim 6 wherein the R¹ and R² independently represent hydrogen, unsubstituted phenyl or $C_1-C_4$ alkoxyphenyl provided that at least one of them is phenyl or alkoxyphenyl.

8. A compound as claimed in claim 7 of the formula

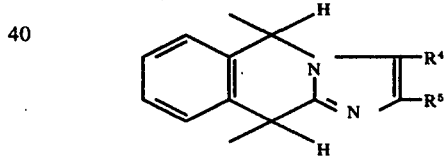

III wherein
R⁴ and R⁵ independently represent phenyl, methoxyphenyl or hydrogen provided that at last one of them is phenyl or methoxyphenyl
or a pharmacologically acceptable nontoxic acid additon salt thereof.

9. A compound as claimed in claim 8 wherein the R⁴ and R⁵ independently represent phenyl, paramethoxy phenyl or hydrogen provided that at least one of them is phenyl or paramethoxyphenyl.

10. The compound of claim 6 which is 2,3-diphenyl-5,10-dihydroimidazo (1,2b) isoquinoline.

11. The compound of claim 6 which is 2,3-di(-paramethoxyphenyl)-5,10-dihydroimidazo (1,2b) isoquinoline.

12. A method of inducing an analgesic, anti-inflammatory or anti-pyretic effect in a patient which comprises administering to the patient an analgesic-, anti-inflammatory- or anti-pyretic- effective amount respectively of a pharmacologically active 5,10-dihydroimidazo (1,2) isoquinoline of the formula

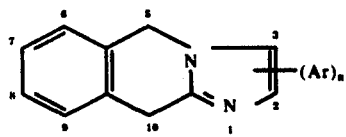

wherein n represents 1 or 2 and

Ar represents a phenyl group or a phenyl group memo substituted as in claim 1, attached by a ring carbon atom thereof to the 2 or 3 position of the dihydro-imidazo-isoquinoline nucleus and, when n represents 2, the groups can be the same or different, or a pharmacologically acceptable nontoxic acid addition salt thereof.

13. A method as claimed in claim 12 wherein said amount is in the range 0.01 to 15 mg/kg body weight.

* * * * *